US00PP12744P2

(12) United States Plant Patent
Dümmen

(10) Patent No.: US PP12,744 P2
(45) Date of Patent: Jul. 2, 2002

(54) POINSETTIA PLANT NAMED 'DUECORED'

(75) Inventor: Marga Dümmen, Rheinberg (DE)

(73) Assignee: Dümmen Jungpflanzenkulturen, Rheinberg (NL)

( * ) Notice: Subject to any disclaimer, the term of this patent is extended or adjusted under 35 U.S.C. 154(b) by 0 days.

(21) Appl. No.: 09/480,599

(22) Filed: Jan. 10, 2000

(51) Int. Cl.[7] ..... A01H 5/00
(52) U.S. Cl. ..... Plt./307

(58) Field of Search ..... Plt./307

*Primary Examiner*—Bruce R. Campell
*Assistant Examiner*—Michelle Kizilkaya
(74) *Attorney, Agent, or Firm*—C. A. Whealy

(57) ABSTRACT

A new and distinct variety of Poinsettia plant named 'Duecored', characterized by its bright red flower bracts; flat to slightly concave flower bracts that are held horizontal or angled slightly upright with respect to stem axis; very dark green foliage; freely branching plant habit; and good post-production longevity.

1 Drawing Sheet

BACKGROUND OF THE INVENTION

The present invention relates to a new and distinct cultivar of Poinsettia plant, botanically known as *Euphorbia pulcherrima* Willd., and hereinafter referred to by the name 'Duecored'.

The new Poinsettia is a naturally-occurring branch mutation of the commercial *Euphorbia pulcherrima* Willd. cultivar Liberty Bright Red, disclosed in U.S. Plant Pat. No. 10,763. The new Poinsettia was discovered and selected by the Inventor in a greenhouse in Rheinberg, Germany.

Asexual reproduction of the new Poinsettia by terminal cuttings taken at Rheinberg, Germany, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Duecored'. These characteristics in combination distinguish 'Duecored' as a new and distinct variety:

1. Bright red flower bracts.
2. Flat to slightly concave flower bracts that are held horizontal or angled slightly upright with respect to stem axis.
3. Very dark green foliage.
4. Freely branching plant habit.
5. Good postproduction longevity.

Plants of the new Poinsettia and the parent cultivar Liberty Bright Red differ primarily in flower bract coloration as flower bracts of the new Poinsettia are more intense and brighter red than flower bracts of the parent cultivar. In addition, plants of the new Poinsettia develop more cyathia per inflorescence than plants of the Liberty Bright Red.

Plants of the new Poinsettia differ from plants of other naturally-occurring branch mutations of 'Liberty Bright Red', namely the cultivars Duecohopi and Duecowi (U.S. Plant Patent applications filed concurrently with this application) primarily in flower bract coloration.

Plants of the new Poinsettia can be compared to plants of the Poinsettia cultivar 490, disclosed in U.S. Plant Pat. No. 7,825. However, in side-by-side comparisons conducted by the Inventor in Rheinberg, Germany, flower bracts of plants of the new Poinsettia are smaller and lighter red in color than flower bracts of plants of the cultivar 490.

BRIEF DESCRIPTION OF THE PHOTOGRAPH

The accompanying colored photograph illustrates the overall appearance of the new Poinsettia, showing the colors as true as it is reasonably possible to obtain in colored reproductions of this type. Colors in the photograph may differ slightly from the color values cited in the detailed botanical description which more accurately describe the actual colors of the new Poinsettia. The photograph comprises a side perspective view of a typical plant of 'Duecored' that was pinched and grown in a 12-cm container.

DETAILED BOTANICAL DESCRIPTION

Plants of the new Poinsettia have not been obseved under all possible environmental conditions. The phenotype may vary somewhat with variations in environment such as temperature, daylength and light intensity, without, however, any variance in genotype. The aforementioned photographs, following observations and measurements describe plants grown in Rheinberg, Germany, under commercial practice in a glass-covered greenhouse with day temperatures about 22° C., night temperatures about 18° C. and light levels about 30 to 40 thousand lux. Plants were grown in 12-cm pots, pinched one time, and flowered under long nyctoperiods. Plants were grown for about 12 weeks after planting rooted cuttings.

In the following description, color references are made to The Royal Horticultural Society Colour Chart except where general terms of ordinary dictionary significance are used.

Botanical classification: *Euphorbia pulcherrima* Willd. cultivar Duecored.

Parentage: Naturally-occurring branch mutation of *Euphorbia pulcherrima* Willd. cultivar Liberty Bright Red, disclosed in U.S. Plant Pat. No. 10,763.

Propagation:

*Type cutting.*—Terminal cuttings.

*Time to initiate roots.*—About 14 days at 22° C.

*Time to develop roots.*—About 21 to 24 days at 22° C.

*Rooting habit.*—Thick, freely branching.

Plant description:

*Plant form.*—Inverted triangle, top of plant rounded.

*Growth habit.*—Freely branching and upright. Branching is enhanced by removing the shoot apex. Moderate growth rate and vigorous. Suitable for 10 to 16-cm containers.

*Plant height.*—About 29 cm.

*Plant spread.*—About 48 cm.

*Crop time.*—From rooted cuttings to a flowering plant in a 12-cm container, about 12 weeks are required.

*Lateral branches.*—Length: About 18 cm. Internode length: About 1.2 cm. Stem/peduncle color: 137A.

*Foliage description.*—Quantity of leaves: About 13 per flowering plant. Length: About 9 cm. Width: About 7 cm. Shape: Deltoid, palmatifid. Apex: Apiculate. Base: Acute. Margin: Entire; incised. Aspect: Slightly concave. Texture: Smooth, glabrous. Color: Young foliage, upper surface: 139A. Young foliage, lower surface: 137B. Mature foliage, upper surface: 139A. Mature foliage, lower surface: 137B. Venation, upper surface: 139A. Venation, lower surface: 138A. Petiole: Length: About 4 cm. Diameter: About 2 mm. Color: 53A and 185A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions.

*Time to flower.*—About six weeks under long nyctoperiod conditions.

*Quantity of inflorescences.*—One per lateral branch, usually about five or six per plant.

*Inflorescence size.*—Diameter: About 25 cm. Height (depth): About 2 cm.

*Flower bract.*—Orientation: Horizontal to angled slightly upright. Quantity of flower bracts per inflorescence: About 17 to 20 per inflorescence. Length: About 10 cm. Width: About 6 cm. Shape: Deltoid. Apex: Apiculate. Base: Acute. Margin: Entire to incised. Texture: Smooth. Color: Developing inflorescence, upper surface: 53B. Developing inflorescence, lower surface: 53C. Mature inflorescence, upper surface: 53B. Mature inflorescence, lower surface: 53C. After senescence, upper surface: 46A.

*Cyathia.*—Quantity: Usually about 12 to 15 per corymb. Diameter of cyathia cluster: About 3.8 cm. Length: About 1 cm. Width: About 6 mm. Color: Immature: 134A. Mature: 143A. Pedicel: Length: About 4 mm. Aspect: Curved. Stamens: Stamen number: About 15 to 20 per cyathium. Anther size: About 1 mm. Anther shape: Rounded. Anther color: 181A. Pollen amount: Moderate. Pollen color: 8B to 8C. Pistils: Pistil number: Typically one per cyathium. Pistil length: About 3 mm. Stigma shape: Trilobate. Stigma color: 181A to 181B. Style length: About 2 mm. Style color: 181B. Quantity of nectaries: One per flower. Nectary color: 15C.

Disease resistance: Plants of the new Poinsettia have not been observed to be resistant to pathogens common to *Euphorbia* when grown under commercial conditions.

Postproduction longevity: Plants generally maintain good substance and bract color for about four to five weeks under interior conditions.

It is claimed:

1. A new and distinct variety of Poinsettia plant named 'Duecored', as illustrated and described.

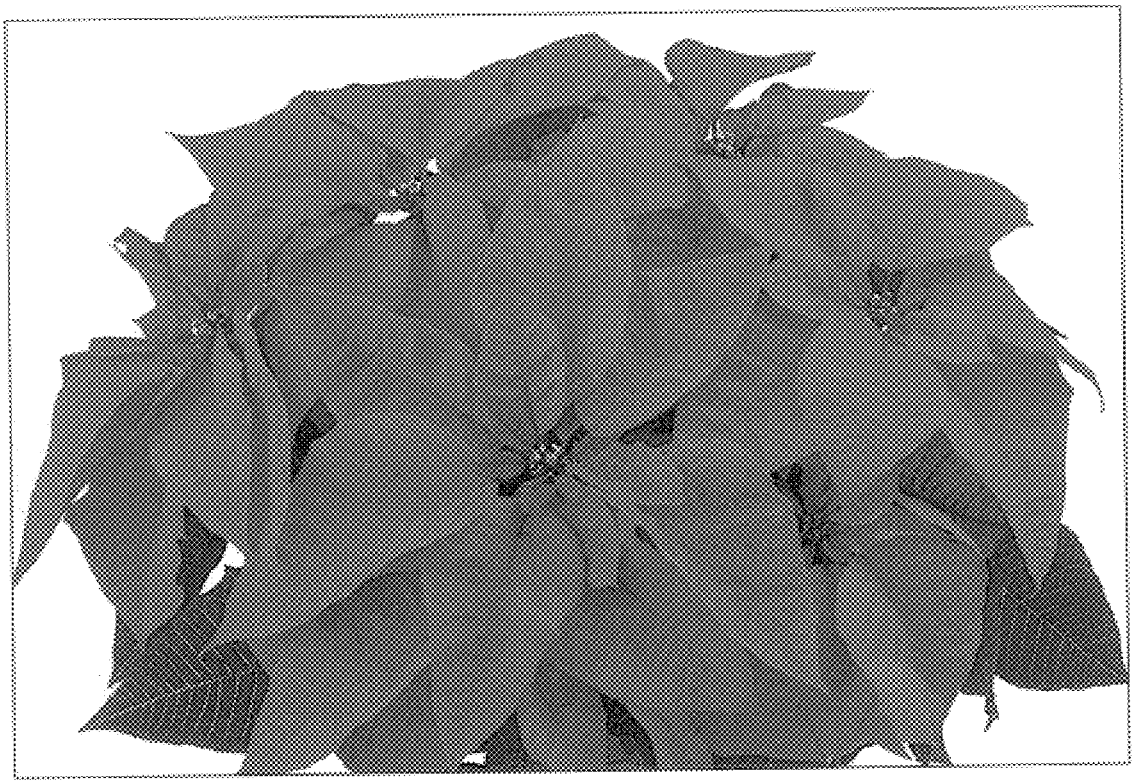

* * * * *